(12) United States Patent
Morazzoni et al.

(10) Patent No.: US 8,591,965 B2
(45) Date of Patent: Nov. 26, 2013

(54) USE OF A GINKGO COMPLEXES FOR THE ENHANCEMENT OF COGNITIVE FUNCTIONS AND THE ALLEVIATION OF MENTAL FATIGUE

(75) Inventors: Paolo Morazzoni, Milan (IT); Orlando Petrini, Ingelheim am Rhein (DE); Andrew Scholey, Ingelheim am Rhein (DE); David Kennedy, Ingelheim am Rhein (DE)

(73) Assignee: Indena S.p.A., Milan (IT)

( * ) Notice: Subject to any disclaimer, the term of this patent is extended or adjusted under 35 U.S.C. 154(b) by 1472 days.

(21) Appl. No.: 10/587,468

(22) PCT Filed: Jan. 26, 2005

(86) PCT No.: PCT/EP2005/000738
§ 371 (c)(1),
(2), (4) Date: Nov. 27, 2006

(87) PCT Pub. No.: WO2005/074956
PCT Pub. Date: Aug. 18, 2005

(65) Prior Publication Data
US 2008/0226757 A1    Sep. 18, 2008

(30) Foreign Application Priority Data
Jan. 29, 2004 (EP) ..................................... 04001937

(51) Int. Cl.
*A61K 36/00* (2006.01)
*A61K 36/16* (2006.01)
*A61K 36/87* (2006.01)

(52) U.S. Cl.
USPC ............................ 424/752; 424/766; 424/725

(58) Field of Classification Search
None
See application file for complete search history.

(56) References Cited

U.S. PATENT DOCUMENTS

| | | | |
|---|---|---|---|
| 6,572,899 B1 | 6/2003 | Gorsek | |
| 6,733,797 B1 * | 5/2004 | Summers | 424/728 |
| 2003/0064118 A1 * | 4/2003 | Petrini et al. | 424/728 |

FOREIGN PATENT DOCUMENTS

| | | |
|---|---|---|
| EP | 0 275 005 | 7/1988 |
| EP | 0 441 279 | 8/1991 |
| WO | WO 03/013549 | 2/2003 |

OTHER PUBLICATIONS

Loew, Value of Ginkgo biloba in treatment of Alzheimer dementia, Wiener medizinische Wochenschrift (1946), (2002) vol. 152, No. 15-16, pp. 418-22. Ref: 40.*
Carini et al, Complexation of Ginkgo biloba extract with phosphatidylcholine improves cardioprotective activity and increases the plasma antioxidant capacity in the rat.*
Kim et al, Proteomics of neuroprotective actions of grape seed extract, FASEB Journal, (Mar. 2003) vol. 17, No. 4-5, pp.*
Introduction of aging from Merck Manuals, accessed on Jul. 28, 2010, pp. 1-3.*
Introduction of Dementia and Alzheimer's disease from Merck manual, accessed on Jul. 28, 2010, pp. 1-18.*
Lee, Treatment of vascular dementia: a comprehensive review, Taehan Sin'gyong Kwahak Hoechi (2003), 21(5), 445-454.*
Jiao et al, Metal-amyloid-.beta. peptide interactions: a preliminary investigation of molecular mechanisms for Alzheimer's disease, Science in China, Series B: Chemistry (2007), 50(4), 453-467.*
Bacskai et al, Four-dimensional multiphoton imaging of brain entry, amyloid binding, and clearance of an amyloid-beta ligand in transgenic mice, Proceedings of the National Academy of Sciences of the United States of America, (Oct. 14, 2003) vol. 100, No. 21, pp. 12462-12467.*
Ashe et al, Molecular basis of memory loss in the Tg2576 mouse model of Alzheimer's disease, Journal of Alzheimer's disease: JAD, (2006) vol. 9, No. 3 Suppl, pp. 123-126.*
Dorner, The Psycho Pathology of Pre Senile Dementias a Survey, Aktuelle Neurologie, (1980) vol. 7, No. 2, pp. 63-73.*
"Phosphatidylserine Complex with Ginkgo" Physiologics, 'Online! 2003, XP002277440 Northglenn, CO, USA, Retrieved from the Internet: URL: http://www.physiologics.com/vf/labels/002632PL.pdf> table of ingredients; product discussion.
Ott B R et al: "Complementary and Alternative Medicines for Alzheimer's Disease" Journal of Geriatric Psychiatry and Neurology, Decker Periodicals, Hamilton, CA, vol. 11, No. 4, Dec. 21, 1998, pp. 163-173, XP001052687 ISSN: 0891-9887 p. 163, left-hand column, lines 8-10; p. 164, left-hand column, lines 19-23; tables 1,2.
Patent Abstracts of Japan vol. 2003, No. 10, Oct. 8, 2003 & JP 2003 169632 A (Sapuri:KK), Jun. 17, 2003 abstract.
Database WPI Section Ch, Week 200314 Derwent Publications Ltd., London, GB; AN 2003-145335 XP002277442 & KR 2002 069 539 A (Doosan Corp) Sep. 5, 2002 abstract.
Kidd P M: "A Review of Nutrients and Botanicals in the Integrative Management of Cognitive Dysfunction" Alternative Medicine Review, Thorne Research Inc., Sandpoint,, US, vol. 4, No. 3, Jun. 1999, pp. 144-161, XP008024312 ISSN: 1089-5159 abstract; figure 2; p. 148, right-hand column, second paragraph; p. 153, left-hand column, first and second paragraphs; p. 154, left-hand column, last paragraph.
Borchers A T et al: "Inflammation and Native American Medicine: The Role of Botanicals" American Journal of Clinical Nutrition, Bethesda, MD, US, vol. 72, No. 2, Aug. 2000, pp. 339-347, XP001083537 ISSN: 0002-9165 abstract; table 1.
Sasaki Keiko et al: "Bilobalide prevents reduction of gamma-aminobutyric acid levels and glutamic acid decarboxylase activity induced by 4-0-methylpyridoxine in mouse hippocampus" Life Sciences, vol. 67, No. 6, Jun. 30, 2000, pp. 709-715, XP002277441 & ISSN: 0024-3205 p. 710, line 8-line 11.

* cited by examiner

*Primary Examiner* — Qiuwen Mi
(74) *Attorney, Agent, or Firm* — Young & Thompson (57) ABSTRACT

The use of *Ginkgo* complexed with phosphatidylserine for the manufacture of a medicament or a dietary supplement for the enhancement of cognitive function and alleviation of mental fatigue, i.e. to improve the speed of memory and memory quality, to increase accuracy and attention in activities in normal healthy subjects, to prevent deterioration of the speed and quality of memory in people with decreased cognitive functions, to counteract cognitive fatigue, and also having an influence on the mood, particularly in healthy children, young adults, middle-aged and/or old people. It is further provided the use of the *Ginkgo*-phosphatidylserine complex for the treatment and prevention of disease related with decreased cognitive function and increased mental fatigue such as Dementia, and Alzheimer's Disease.

19 Claims, 6 Drawing Sheets

USE OF A GINKGO COMPLEXES FOR THE ENHANCEMENT OF COGNITIVE FUNCTIONS AND THE ALLEVIATION OF MENTAL FATIGUE

FIELD OF THE INVENTION

The present invention relates to a novel use of a *Ginkgo* complex for the enhancement of cognitive function and mental fatigue functions.

BACKGROUND OF THE INVENTION

The isolation of a lactone compound $C_{15}H_{18}O_8$ from the leaves of *Ginkgo biloba*, to which the name bilobalide was given, was first mentioned in 1967 by R. T. Major (Science 157 (1967), p. 1270-1273). The structural formula for said bilobalide was already proposed in 1971 (J. Amer. Chem. Soc. 93 (1971), p. 3544-3546) and is as follows:

The active main components of *Ginkgo* are alkylated phenoles such as ginkgol and 3-(8-pentadecenyl) phenol, and phenolic carboxylic acids such as 2-hydroxy-6-(8-pentadecenyl) benzoic acid, ginkolide and bilobalide. Bilobalide, a sesquiterpene, and ginkgolide, a hexacyclic diterpene, are the only known naturally occurring compounds having tert. butyl groups. Said substances may be isolated from the leaves and other organs of the *Ginkgo biloba* tree, e.g. bilobalide is found in the leaves of *Ginkgo biloba* at concentrations below 0.01%.

The known extracts have been used for the treatment of disturbances of cerebral and peripheral arterial blood flow. The contained ginkgo-flavone glycosides and terpenoids are known to have vaso-regulating and blood viscosity decreasing properties. The main indications for which *Ginkgo* is prescribed in Western countries, such as France and Germany, is cerebral insufficiency. Further, *Ginkgo biloba* has been extensively used for various indications in Chinese medicine and is described in the traditional Chinese Pharmacy.

In recent years also complexes between natural or synthetic phospholipids and bilobalide, as well as preparations thereof, have been investigated. The U.S. Pat. No. 5,043,323, for example, discloses complex compounds of bioflavonoids with phospholipids, including *Ginkgo biloba* complexed with phosphatidyl serine.

Furthermore, the U.S. Pat. No. 5,202,313 suggests their therapeutic application as antiinflammatory agents and as agents for the treatment of disorders associated with inflammatory or traumatic neuritic processes.

Moreover *Ginkgo* extracts are known to have effects on cognitive functions. For example V. D. Petkov et al., Planta Med. 59 (1993), pp. 106-114, disclose that the standardized extracts of *Panax ginseng, Ginkgo biloba* and a combination thereof improve the learned behavior of young and old rodents.

According to the teaching of WO 01/43753 A2 it was found in cognitive tests that administering a combination of extracts of the root of *Panax ginseng* and of the leaves of *Ginkgo biloba* to humans positively effects cognitive skills, for example the speed and quality of memory in normal healthy subjects.

Furthermore, there has been a variety of studies on the influence of *ginkgo biloba* extract on cognitive performance. It has been suggested (Moss and Scholey 1996, Scholey et al 1999, Kennedy and Scholey 2000) that some demanding cognitive tasks may be facilitated by the simple augmentation of delivery of metabolic substrates to the brain. As an example, a previous study from this laboratory (Kennedy and Scholey 2000) investigated the relationship between heart rate, blood glucose levels and performance on a "demanding" mental arithmetic task (serial verbal subtraction of 7 from a given number between 800 and 1000), a "less demanding" mental arithmetic task (serial subtraction of 3), and a long term verbal memory task. It was found that not only both serial subtraction tasks engendered significant increases in heart rate above that engendered by somatically identical counting tasks, but that performance on both was also related to the magnitude of fall in blood glucose levels during task performance. Performance on the most demanding task (serial 7s) was also not only improved by a glucose drink, but was also related to resting heart rate.

However the effects according to the use of the inventive complex are superior and of a novel type.

SUMMARY OF THE INVENTION

Unexpectedly, it has been found by the present inventors that a *Ginkgo biloba* extract complexed with phosphatidyl serine may be used to enhance significantly above the levels provided by the non-complexed extract cognitive function and mental fatigue, which comprises the administration of a medicament and/or a dietary supplement containing *Ginkgo* in the complexed form. The *Ginkgo* complex may be used for the enhancement of cognitive function and mental fatigue in healthy people, in particular children or young adults.

Another aspect of the present invention is the possibility to prevent deterioration of the speed of memory in people with decreased cognitive functions and to counteract cognitive fatigue.

A further aspect of the present invention is the maintenance of healthy cognitive functions and delay of age-related cognitive decline in middle-aged and/or old people, particularly healthy middle-aged and/or healthy old people.

Still another aspect of the present invention is the possibility of providing a medicament or a dietary supplement for the treatment and prevention of a disease related with a decrease of the cognitive function and mental fatigue such as Dementia, e.g. Alzheimer's disease.

It is therefore a primary object of the present invention to provide the use of an active composition to enhance the cognitive function and mental fatigue, i.e. to improve the factors related therewith such as to improve the speed of memory and memory quality, to increase accuracy and attention in activities in normal, healthy subjects, to prevent deterioration of the speed and quality of memory in people with decreased cognitive functions and to counteract cognitive fatigue, also having an influence on the mood, particularly in healthy children, young adults, middle-aged and/or old people.

It is a further object of the present invention to provide the use of an active composition for improving cognitive skills and/or mental effort by taking formulations comprising ingredients of natural origin, wherein the constituents are manufactured pursuant to a controlled process that preserves the curing qualities of the ingredients.

It is still a further object of the present invention to provide the use of an active composition comprising constituents of natural origin and having minimal or no side effects and thus being safe for internal consumption.

It is a further object of the present invention to provide the use of an active composition for the treatment and prevention of a disease related with a decrease of the cognitive function and mental fatigue such as Dementia, e.g. Alzheimer's disease.

Furthermore, the invention relates to a pharmaceutical or dietary composition comprising a *Ginkgo biloba* extract complexed with phosphatidyl serine, at least one vitamin, optionally one or more minerals and trace elements and a pharmaceutically or dietarily acceptable carrier.

Finally, the invention relates to a *Ginkgo biloba* extract complexed with a certain phosphatidyl serine with a defined ratio of different fatty acids.

DESCRIPTION OF THE INVENTION

The present invention refers to the use of *Ginkgo* complexed with phosphatidylserine for the manufacture of a medicament or dietary supplement for the enhancement of cognitive function and mental fatigue. The *Ginkgo* used is derived from the plant *Ginkgo biloba*, and represents an extract or extracts thereof and/or the principal active substances thereof.

Under the term *Ginkgo* phosphatidylserine complex or abbreviated *Ginkgo*-PS is meant a complex obtainable from a reaction of the active ingredients of an extract of *Ginkgo* with a phospholipid containing from 10 to 50%, preferably from 20 to 40%, more preferably 20% of phosphatidylserine.

Under the term "extract" is meant that the plants or plant components are extracted with a suitable solvent like water, ethanol, a mixture thereof, oils or any other suitable solvent well known in the state of the art of extracting plants. These extracts can be used as such if pharmacologically acceptable or the solvent of the resulting solutions is removed and the residue is used as such or after further worked up, for example after resolving or re-suspending in a pharmacologically suitable solvent.

Under the term "principal active substances" is meant the active ingredients that are mainly responsible for the pharmacological effect. Preferably the formulation comprises all those ingredients of the plant of interest that are responsible for at least about 75 percent, more preferably at least about 90 percent of the pharmacological effects. These active ingredients may be won from the plants or synthesized chemically.

As used herein a "pharmacologically acceptable" component is one that is suitable for use with humans without undue adverse side effects such as toxicity, irritation and allergic response, commensurate with a reasonable benefit/risk ratio.

Complexes between natural or synthetic phospholipids and bilobalide are known from prior art (e.g. U.S. Pat. No. 5,043,323 and U.S. Pat. No. 5,202,313), as well as the preparation thereof and their therapeutic application as anti-inflammatory agents and as agents for the treatment of disorders associated with inflammatory or traumatic neuritic processes. Bilobalide forms with phospholipids new compounds, which exhibit a different bioavailability compared with free bilobalide and are suitable for incorporation into pharmaceutical formulations.

The complex between the flavonoids from *Ginkgo biloba* and phophatidylserine is prepared analogously as described in examples 6 of U.S. Pat. No. 5,043,323.

Preparation of *Ginkgo biloba* extract soy phosphatidylserine complex.

1.87 kg of 20% phosphatidylserine were suspended at room temperature in 17.5 L of ethyl acetate. *Ginkgo biloba* dry extract (0.65 kg) was added and stirring. The suspension was kept under stirring at reflux for 1 hour.

The suspension was filtered at 70-75° C. and the mother liquors concentrated at ambient pressure until a soft residue is obtained.

The residue was dried at 40° C. for 48 hours. Yields: 2.23 kg of *Ginkgo biloba* extract phosphatidylserine complex.

Therefore, the formation of *Ginkgo* phospholipid complexes enables the preparation of new biologically active compositions. In fact, they possess physico-chemical and spectroscopic characteristics which are markedly different from those of the original components and as such they can be incorporated as active principles into pharmaceutical formulations. *Ginkgo* shows a strong affinity for phospholipids, resulting in the generation of bonds which markedly modify the physico-chemical and spectroscopic characteristics of the new molecules. The formation of the complex will be confirmed for example by nuclear magnetic resonance analysis, which enables the identification of the interaction between the reacting molecular species and the portion of the molecule which is involved in the reaction.

Specifically, the complex of the present invention comprises herbal ingredients for example derived by an extraction from *Ginkgo* leaves. The *Ginkgo* extract contains among other substances ginkgo flavone glycosides and terpene lactones. Another possibility is that the formulation comprises dried *Ginkgo* leaves or other plant components, that optionally are powdered. Under the term "plant" is understood the plant itself as well as plant parts comprising the active ingredients. Like for example leaves, stems, fruits or roots as mentioned above. Preferably the plant or plant components are dried. Optionally, they may be powdered.

While all these substances present in *Ginkgo* are known to have pharmacological activities, the range of their pharmacological actions has not yet been fully elucidated, but in-vitro studies indicate that some of them have antioxidant properties and that they inhibit platelet aggregation, while others exert an action on the oxygen uptake in the cells and others again may exert an immunomodulating action.

In a preferred embodiment the *Ginkgo* extract used contains among other substances ginkgo flavone glycosides and terpene lactones, preferably containing at least about 20%, preferably about 21.0 to about 30%, in particular about 22.0 to about 27.0% ginkgo flavone glycosides and about 2 to about 10%, preferably about 4.0 to about 8.0%, in particular about 5.0 to about 7.0%, most preferably about 6% terpene lactones. Preferably the medicament and/or dietary supplement comprises *Ginkgo* extract containing at least about 24% ginkgo flavone glycosides and about 6% terpene lactones. In particular *Ginkgo* extract disclosed in EP 0360556 is used as basis to produce the complex.

The phospholipids used for the preparation of the complexes may be either natural or synthetic. The natural phospholipids are normally those extracted from soy-bean or from animal organs, whereas the synthetic phospholipids have homogeneous acyl chains and are prepared according to methods described in prior art.

According to the present invention the phospholipid selected for the preparation of the complex is a phospholipid containing from 10 to 50% of phosphatidylserine. Preferably the phospholipid contain from 20 to 40% and particular preferred about 20% of phosphatidylserine of formula wherein R and R[1] each independently represent an $C_{6-20}$ acyl group, preferably an acyl moiety selected from the group consisting of palmitoyl, oleoyl, linoleoyl, linolenoyl, in particular which comprises, on an average, from 15 to 25% of saturated fatty acids, from 5 to 15% of mono-unsaturated fatty acids and from 60 to 80% of polyunsaturated fatty acids, based on the total acids; and R[2] represents the residue of serine.

The reaction of *Ginkgo* with phosphatidylserine under appropriate conditions results in the generation of a product whose physico-chemical characteristics are completely different from those of the individual constituents.

The resulting complex is lipophilic in character and is soluble in nonpolar and aprotic solvents, in which the individual components of the complex are normally insoluble.

The resulting complex exhibits a greater activity as compared to *Ginkgo* in free form and are suitable for incorporation into the most common pharmaceutical formulations.

The complexes described in the present invention may be prepared by reacting in proper solvents, such as hot cyclic ether, aromatic hydrocarbons, halogen derivatives or methanol-methylene chloride mixture. It is therefore preferred that the ratio between *Ginkgo* and the phospholipid used to prepare the complex is about 0.5-1:2-5, preferably 1:3 W/w. The final products are then isolated by evaporation of the reaction solvent or by precipitation of the complex with appropriate solvents. The complex may also be prepared by lyophilizing the product obtained from the reaction of the components in dioxane.

The production of the complex used according to the present invention provides a useful mode of administration for *Ginkgo*, the principal active substances or extracts thereof. The possibility of producing new structures with *Ginkgo* extracts which retain unaltered the structure of the basic compound but exhibit a several-fold increase in a specific activity represents a significant advantage for the novel use which certainly could not be predicted beforehand. Due to the enhancement in the specific activity used, it is possible to reduce the dosage having the known benefits.

It has been unexpectedly found that the complex used according to the present invention has a direct influence on the cognitive function and mental fatigue. The expression "cognitive performance" involves but is not limited to improve factors related therewith such as improved speed of memory and memory quality, improved reaction time and working memory, increased accuracy and attention in activities in normal, healthy subjects, to prevent deterioration of the speed and quality of memory in people with decreased cognitive functions and to counteract cognitive fatigue having an influence on the mood and the physical well-being, particularly in healthy children, young adults, middle-aged and/or old people. It could be demonstrated that the ginkgo phosphatidylserine complex used according to the present invention has an excellent influence and effectivity on cognitive function and mental fatigue and the related cognitive factors such as quality of memory, speed of memory, and the majority of the activities concerning attention and accuracy. The general context will be clear from the study explained in the experimental part.

The complex can be used at dosages ranging from about 20 to about 240 mg/day, preferably about 60 to about 120 mg/day, particularly preferred from about 80 to about 100 mg/day in single or divided daily administrations as medicament or as a dietary supplement.

The medicament or dietary supplement may be in the form of tablets, coated tablets, granules, powders, powders in capsules, syrups, solutions or suspensions for example on the basis of water, ethanol or a mixture thereof, dragees, gels, injections or any other suitable manner well known to the skilled person. These products may be administered also as topical formulations, at variable dosages depending on the desired application, e.g. the severity of the pathological condition being treated. Preferably, the medicament and/or dietary supplement is administrated in a form suitable for oral administration, such as granules, tablets, capsules, drops, syrups or others.

The term "dietary supplement" as used hereinabove and hereinbelow includes a composition which may be used without prescription by a third party, for example a physician. The components may be taken together with meals or separated thereof, on a daily basis or only sometimes. Dietary supplements are primarily important for those having inadequate diets, individuals with a reduced ability to utilize or absorb the essential substances from food, particularly the elderly persons.

According to a preferred embodiment of the present invention the *Ginkgo* phosphatidylserine complex may be used with a suitable or pharmacologically acceptable amount of additives. Such additives may be, but are not limited to minerals, vitamins, sweeteners, flavors, pharmaceutically acceptable carriers, auxiliary and binder agents, excipients and mixtures thereof.

The minerals used may be for example selected from salts of calcium, copper, magnesium, iron, zinc, iodine, selenium, manganese, fluoride, chromium, molybdenum, sodium, potassium, chloride and mixtures thereof. Additional minerals which are less preferred are arsenic, nickel, silicon, boron, cadmium, lead, lithium, tin, vanadium and cobalt salts and mixtures thereof. The mineral sources are usually present in nutritionally relevant amounts. The source of the mineral salts used maybe any of the well known salts such as carbonate, oxide, hydroxide, chloride, sulfate, phosphate, gluconate, lactate, acetate, fumarate, citrate, malate, amino acids and the like for the cationic minerals and sodium, potassium, calcium, magnesium and the like for the anionic minerals. Those skilled in the art are familiar with the preferred ranges for infants or adults, depending somewhat on age and physiological state. It is clear that the daily intake of minerals may vary with the user so that no exact dosages may be mentioned. According to the present invention it is most preferred that the following minerals present in the medicament or dietary supplement may be selected from calcium, fluorine, phosphorus, copper, potassium, manganese, magnesium selenium, zinc and iron.

Vitamins which may optionally be used according to the present invention can be, but are not limited to water-soluble vitamins e.g. Vitamin C e.g. L-(+)-ascorbic acid, calcium ascorbate, potassium ascorbate, 6-palmitoyl-L-ascorbic acid; Vitamin B1 e.g. thiamine hydrochloride, thiamine mononitrate; Vitamin B2 e.g. riboflavin, riboflavin 5'-phosphate sodium; Vitamin B6 e.g. pyridoxine hydrochloride, Vitamin B12 e.g. cyanocobalamine; Vitamin H e.g. D-biotin; Folic Acid; Vitamin PP (Niacin) e.g. nicotinamide, nicotinic acid;

pro Vitamin B5 e.g. panthenol (d and dl forms) ethyl panthenol and calcium D-pantothenate; and fat-soluble vitamins e.g. Vitamin A e.g. Vitamin A palmitate, Vitamin A acetate, Vitamin A propionate, all trans retinol; Vitamin D e.g. ergocalciferol, cholecalciferol, cholecalciferol-cholesterol; Vitamin E e.g. alpha-tocopherol, alpha-tocopheryl acetate, alpha-tocopheryl acid succinate (d and dl forms); Vitamin K such Vitamin K1 e.g. phytomenadione, and Carotene (provitamin) e.g. lycopene, zeaxanthin, lutein, alpha-carotene, beta-carotene, apocarotinal, gamma-carotene and beta-cryptoxanthin, derivatives and mixtures thereof. The vitamins may be present in nutritional relevant amounts depending on age and physiological state as already mentioned above. Preferred vitamins are vitamin A, vitamins B1, B2 and B12, vitamin C, vitamin D2, nicotinamide, calcium pantotenate, rutoside and vitamin E.

Further additives in medicaments or dietary supplements which may optionally be present belong to basic knowledge of the skilled person and shall not be discussed in detail.

According to the present invention it is particularly preferred if minerals and/or vitamins are present as additives. Such a combination of the *Ginkgo* phosphatidylserine complex and selected multivitamins and/or minerals is particularly suitable for maintaining and/or restoring cognitive functions and improving physical well-being, for example in elderly persons or patients. Thus, the *Ginkgo* complex combined with a multivitamin/minerals formulation may be tailored particularly to the needs of elderly persons who face or want to prevent age-related decline of cognitive functions and physical well-being. It is a meaningful combination of *Ginkgo* and phosphatidylserine in form of a complex which is proven in the experimental part to have strong beneficial effects on cognitive function. The performance may be increased with additives such as minerals and/or vitamins which are selected and dosed according to their potential of maintaining and restoring cognitive functions and improving physical well-being, particularly of elderly persons. Most preferred is a combination consisting essentially of:

a complex of *Ginkgo* extract and phosphatidylserine
Vitamin A
Vitamin B1
Vitamin B2
Vitamin B6
Vitamin B12
Vitamin C
Vitamin D2
Vitamin E
Nicotinamide
Calcium Pantotenate
Rutoside
Folic Acid
Fluorine
Calcium
Phosphorus
Copper
Potassium
Manganese
Magnesium
Zinc
Iron
Lecithin Therefore, the complex according to the present invention may be used for the improvement of cognitive functions in healthy young people and the maintenance of healthy cognitive functions and delay of age-related cognitive decline in healthy middle-aged and/or old people. However, according to a further embodiment the complex may be used for manufacturing a medicament or a dietary supplement for the treatment and prevention of diseases related with the reduction of cognitive function and mental fatigue.

Still a further aspect of the present invention is directed to the use of *Ginkgo* complexed with phosphatidylserine for the manufacture of a medicament or a dietary supplement for the treatment and prevention of Dementia, e.g. Alzheimer's disease.

It is preferred that the medicament or dietary supplement additionally contains a pharmaceutically acceptable amount of at least one additive which may be selected from the group comprising vitamins, minerals, sweeteners, flavors, pharmaceutically acceptable carriers, auxiliary and binder agents, excipients and mixtures thereof, as already described.

In a preferred embodiment the complex of the present invention may also be used in combination with an additionally active compound, i.e. the *Ginkgo* complex may also play a role in the combination treatment of Dementia such as age-related Dementia, e.g. Alzheimer's Disease. An active compound in this connection may be a pharmaceutical compound or another active substance used for the treatment and prevention of the disease to be treated, e.g. a compound which supports the treatment and curing of Alzheimer's Disease.

One example of said embodiment of the invention may be to use *Ginkgo* complexed with phosphatidylserine of the invention as adjuvant therapy in the treatment of Dementia particularly Alzheimer's disease in combination with acetylcholinesterase inhibitors. The leading acetylcholinesterase inhibitors in the treatment of Dementia are Donepezil (Aricept® available from Pfizer), Rivastigmine (Exelon® available from Novartis) and Galantamine (Reminyle available from Johnson & Johnson). Therefore the complex of the present invention may be co-administered with such a known acetylcholinesterase inhibitor. In this context under the term "co-administration" is meant that each of the two components (complex and additional active compound) are administered at the same time or separately but within a close timely relationship.

A further embodiment for the combined therapy with the inventive complex and an additionally active compound is the combination treatment in an age-related Dementia such as Alzheimer's Disease by the co-administration of the complex of the present invention and complexed grape seed extract as additionally active compound. It has been found that the combined use of the inventive complex and an additionally active compound leads to superior results in the prevention or curing of such diseases and supports to alleviate the symptoms and to extenuate the course of the disease in an extraordinary way.

DETAILED DESCRIPTION OF THE INVENTION

In a pilot study in form of a randomised, double-blind, balanced crossover study the influence of several preparations on cognitive skills was conducted. In this study, the effects and influence of a ginkgo phosphatidylcholine complex, ginkgo phosphatidylserine complex, not complexed ginkgo and an inert placebo have been compared and evaluated.

It will be readily apparent to those skilled in the art that various changes and modifications of an obvious nature may be made without departing from the spirit of the invention, and all such changes and modifications of an obvious nature may be made without departing from the spirit of the invention, and all such changes and modifications are considered to fall within the scope of the invention, as defined by the claims. While the use of the complex of the present invention has been set forth in what is believed to be preferred embodiments, it is recognized that departures may be made within the spirit and scope of the following claims which, therefore, should not be limited except within the doctrine of equivalents.

METHOD

Cognitive Assessment
Participants 19 female and 9 male undergraduate volunteers (mean age 21.4 years, Standard Deviation 4.1 years) took part in the study which was approved by the Joint Ethics Committee of Newcastle and North Tyneside Health Authority and was carried out in accordance with the Declaration of Helsinki. Prior to participation each volunteer signed an informed consent form and completed a medical health questionnaire. All participants reported that they were in good health, and were taking no illicit social drugs. Additionally they were free of any "over the counter" or prescribed medications, with the exception, for some female volunteers, of the contraceptive pill. Regular smokers were excluded from the study. All participants abstained from alcohol for a minimum of 12 hours prior to the first testing session of the morning.

Cognitive Drug Research (CDR) Computerised Assessment Battery

The Cognitive Drug Research (CDR) computerised assessment battery has been used in hundreds of European and North American drug trials, and has been shown to be sensitive to acute cognitive improvements (e.g. Moss et al 1998; Scholey et al 1999) as well as impairments with a wide variety of substances (e.g. Ebert et al 1998; O'Neill et al 1995).

A tailored version of the CDR battery was used. This has previously been found to be sensitive to modulation of cognitive function as a consequence of acute ingestion of *Melissa officinalis* Kennedy et al, 2002b), *Ginkgo biloba* (Kennedy et al 2000; 2002a) and *Panax ginseng* (Kennedy et al 2001a; 2002a), and acute and chronic administration of a *Ginkgo biloba/Panax ginseng* combination (Kennedy et al 2001 b; 2002a; Wesnes et al 1997; Wesnes et al 2000). In the case of the current study the additional rapid visual information processing (RVIP) task was included in the battery. The selection of computer controlled tasks from the system was administered with randomly ordered parallel forms of the tests being presented at each testing session. Presentation was via desktop computers with high resolution VGA colour monitors, and, with the exception of written word recall tests, all responses were recorded via two-button (YES/NO) response boxes. The entire selection of tasks took approximately 20 minutes to perform.

Tests were administered in the following order:

Word Presentation: Fifteen words, matched for frequency and concreteness, were presented in random order on the monitor for the participant to remember. Stimulus duration was 1 second, as was the interstimulus interval.

Immediate Word Recall: The participant was allowed 60 seconds to write down as many of the words as possible. The task was scored as number of words correct and the resulting score was converted into a percentage.

Picture Presentation: A series of 20 photographic images of everyday objects and scenes were presented on the monitor at the rate of 1 every 3 seconds, with a stimulus duration of 1 second, for the participant to remember.

Simple Reaction Time: The participant was instructed to press the "YES" response button as quickly as possible every time the word "YES" was presented on the monitor. Fifty stimuli were presented with an inter-stimulus interval that varied randomly between 1 and 3.5 seconds. Reaction times were recorded in msecs.

Digit Vigilance Task: A target digit was randomly selected and constantly displayed to the right of the monitor screen. A series of digits was presented in the centre of the screen at the rate of 80 per minute and the participant was required to press the "YES" button as quickly as possible every time the digit in the series matched the target digit. The task lasted one minute and there were 15 stimulus-target matches. Task measures were accuracy (%), reaction time (msecs) and number of false alarms.

Choice Reaction Time: Either the word "NO" or the word "YES" was presented on the monitor and the participant was required to press the corresponding button as quickly as possible. There were 50 trials, of which the stimulus word was chosen randomly with equal probability, with a randomly varying inter-stimulus interval of between 1 and 3.5 seconds. Reaction times (msec) and accuracy (%) were recorded.

Spatial Working Memory: A pictorial representation of a house was presented on the screen with four of its nine windows lit. The participant was instructed to memorise the position of the illuminated windows. In 36 subsequent presentations of the house, one of the windows was illuminated and the participant decided whether or not this matched one of the lighted windows in the original presentation. The participant made their response by pressing the "YES" or "NO" response button as quickly as possible. Mean reaction times were measured in msec, and accuracy of responses to both original and novel (distractor) stimuli were recorded as percentages which were used to derive a "% greater than chance performance" score (percentage of original targets+percentage of novel targets correctly identified—100).

Numeric Working Memory: Five digits were presented sequentially for the participant to hold in memory. This was followed by a series of 30 probe digits for each of which the participant decided whether or not it had been in the original series and pressed the "YES" or "NO" response button as appropriate as quickly as possible. This was repeated two further times with different stimuli and probe digits. Mean reaction times were measured in msec, and accuracy of responses to both original and novel (distractor) stimuli were recorded as percentages which were used to derive a "% greater than chance performance" score as above.

Delayed Word Recall: The participant was again given 60 seconds to write down as many of the words as possible. The task was scored for number of words correct and the resulting score was converted into a percentage.

Delayed Word Recognition: The original words plus 15 distractor words were presented one at a time in a randomised order. For each word the participant indicated whether or not be recognised it as being included in the original list of words by pressing the "YES" or "NO" button as appropriate and as quickly as possible. Mean reaction times were measured in msec, and accuracy of responses to both original and novel (distractor) stimuli were recorded as percentages which were used to derive a "% greater than chance performance" score as above.

Delayed Picture Recognition: The original pictures plus 20 distractor pictures were presented one at a time in a randomised order. For each picture participants indicated whether or not it was recognised as being from the original series by pressing the "YES" or "NO" button as appropriate and as quickly as possible. Mean reaction times were measured in msec, and accuracy of responses to both original and novel (distractor) stimuli were recorded as percentages which were used to derive a "% greater than chance performance" score as above.

Primary Cognitive Outcome Measures

The above measures were collapsed into the "Quality of Memory" measure and five cognitive outcome factors derived from the battery by a factor analysis conducted by Wesnes et al (2000). These measures have been utilised in a number of studies, including a several assessing the cognitive effects of herbal remedies (Kennedy et al, 2000; 2001a; 2001b; 2002a; 2002b; Wesnes et al, 1997; 2000). The original factor analysis of data from the battery is described in detail in Wesnes et al (2000).

Attention

"Speed of Attention" factor: derived by combining the reaction times of the three attentional tasks—simple reaction time, choice reaction time and digit vigilance (units are summed milliseconds for the 3 tasks).

"Accuracy of Attention" factor: derived by calculating the combined percentage accuracy across the choice reaction time and digit vigilance tasks with adjustment for false alarms from the latter test. 100% accuracy across the two tasks would generate a maximum score of 100.

Memory

"Speed of Memory" factor: derived by combining the reaction times of the four computerised memory tasks—numeric working memory, spatial memory, delayed word recognition, and delayed picture recognition (units are summed milliseconds for the 4 tasks).

"Quality of Memory" measure: derived by combining the "Secondary Memory" and "Working Memory" factor scores (see below).

"Secondary Memory" factor: derived by combining the percentage accuracy scores (adjusted for proportions of novel and original stimuli where appropriate) from all of the secondary memory tests—delayed word recognition, delayed picture recognition, immediate word recall and delayed word recall (with adjustments to the total % correct for errors and intrusions on the latter two tasks). One hundred percent accuracy across the four tasks would generate a maximum score of 400 on this index.

"Working Memory" factor: derived by combining the percentage accuracy scores from the two working memory tests—spatial working memory, and numeric working memory. One hundred percent accuracy across the two tasks would generate a maximum score of 200 on this index.

Serial 3s and 7s Subtraction Tasks

A modified computerised version of the Serial Sevens test was utilised. The original verbal Serial Sevens test (Hayman, 1942) has appeared in a number of forms, including as part of the Mini-Mental State Examination (Folstein et al, 1975). It has been used to assess cognitive impairment during hypoglycaemia (e.g. Hale et al, 1982; Taylor and Rachman, 1988), and has also been used to investigate the relationship between increased blood glucose levels and cognitive performance (Kennedy and Scholey, 2000; Scholey et al, 2001; Scholey, 2001). In the current studies, computerised versions of serial subtractions were implemented (see Scholey et al, 2001 for details), here using tests of 2 minutes duration. For the Serial Sevens task a standard instruction screen informed the participant to count backwards in sevens from the given number, as quickly and accurately as possible, using the numeric keypad to enter each response. Participants were also instructed verbally that if they were to make a mistake they should carry on subtracting from the new incorrect number. A random starting number between 800 and 999 was presented on the computer screen, which was cleared by the entry of the first response. Each three-digit response was entered via the numeric keypad with each digit being represented on screen by an asterisk. Pressing the enter key signalled the end of each response and cleared the three asterisks from the screen. The task was scored for total number of subtraction and number of errors. In the case of incorrect responses, subsequent responses were scored as positive if they were correct in relation to the new number.

The Serial Threes task was identical to Serial Sevens, except that it involved serial subtraction of threes.

Subjective Mood Measure

The Bond-Lader Visual Analogue Scales (Bond and Lader 1974), consisting of 16 100 mm visual analogue scales anchored by antonyms (e.g. Alert-Drowsy, Lethargic-Energetic, etc) were combined as recommended by the authors to form three mood factors: alertness, calmness and contentedness.

Treatments

On each study day participants received two capsules that were of identical appearance on each occasion. The individual capsules contained either an inert placebo, 60 mg *Ginkgo biloba* extract, 180 mg of *Ginkgo biloba* extract complexed with phosphatidylcholine (equivalent to 60 mg of *Ginkgo biloba* extract, in the following referred to as "PC"), or 240 mg of *Ginkgo biloba* extract complexed with phosphatidylserine (phospholipid containing 20% of phospatidylserine. The complex is equivalent to 60 mg of *Ginkgo biloba* extract and in the following is referred to as "PS"). Depending on the condition to which the participant was allocated on that particular day the combination of capsules corresponded to a dose of either 0 mg (placebo), 120 mg ginkgo, 360 mg ginkgo complexed with phosphatidylcholine, or 480 mg ginkgo complexed with phospholipid containing 20% of phosphatidylserine. To maintain the double blind, coded treatments were provided by the manufacturer in identical hard gelatine capsules. A disinterested third party was then responsible for preparing treatments as per the study's Latin Square. The code remained unbroken until initial statistical analysis had been completed. All treatments were identical in appearance and scent.

Procedure

Each participant was required to attend a total of five study days that were conducted seven days apart, to ensure a sufficient wash-out between conditions. Testing took place, commencing at the same time on each day, in a suite of laboratories with participants visually isolated from each other.

On arrival at their first session on the first day participants were randomly allocated to a treatment regime using a Latin Square design which counterbalanced the order of treatments across the four active days of the study.

The first day was identical to the following four, except that no treatment (active or placebo) was offered, to allow familiarisation with the test battery and procedure. Data from the four sessions of this practice day were not included in any analysis. Each active study day comprised four identical testing sessions. The first was a pre-dose testing session which established baseline performance for that day, and was immediately followed by the day's treatment on days 2 to 5. Further testing sessions began at 1 hour, 3 hours, and 6 hours following consumption of the day's treatment.

Each testing session comprised completion of the Bond-Lader visual analogue scales, and the CDR test battery.

Statistics

Scores on the individual task outcomes, the four primary factors and the two memory sub-factors were analysed as "change from baseline" using the Minitab statistical package.

Prior to carrying out planned comparisons, an ANOVA (General Linear Model), with terms fitted to the model for dose, visit, dose x visit and subject (Kirk 1968), was carried out to identify main effects and interaction effects on change from baseline data for each measure. The primary statistical analysis of the "change from baseline" data for each measure was carried out using planned comparisons, utilising t tests with the mean squares for "Dose*Time*Subjects" from an omnibus ANOVA as an error term (Keppel 1991). At each time point (1, 2.5, 4 and 6 hours post-dose) data from the placebo condition was compared to that for each of the three treatments (ginkgo, ginkgo+PC (phosphatidylcholine), ginkgo+PS (phosphatidylserine)). To ensure the overall Type I error protection level only those planned comparisons associated with measures that generated a significant main effect or interaction effect on the initial ANOVA are reported. Furthermore, all testing was two-tailed, comparisons were strictly planned prior to the study, were restricted to the number of conditions minus one at each time-point, and only probabilities associated with these pre-planned comparisons were calculated.

Results

Cognitive Assessment

Baseline Scores

Prior to analysis of change from baseline data, mean pre-dose raw baseline scores for all four conditions (placebo, ginkgo, ginkgo+PC, ginkgo+PS) for each outcome (single task outcomes, cognitive factor scores, and mood scale scores) were subjected to a one-way, repeated-measures ANOVA followed, for measures generating a significant result, by planned comparisons as per the cognitive outcome data. Several single task outcomes generated significant pre-dose baseline differences on the planned comparisons. Prior to ingestion of the days treatment participants in the ginkgo+PS condition performed significantly less accurately [t (81) =2.32, p=0.022] and more slowly [t (81)=2.75, p=0.007] than placebo on the Digit vigilance task. The same condition performed significantly slower on the Word recognition task [t (81)=2.11, p=0.036]. No other planned comparisons proved significant for any other measure.

Individual Task Outcome Measures

Figure 1:
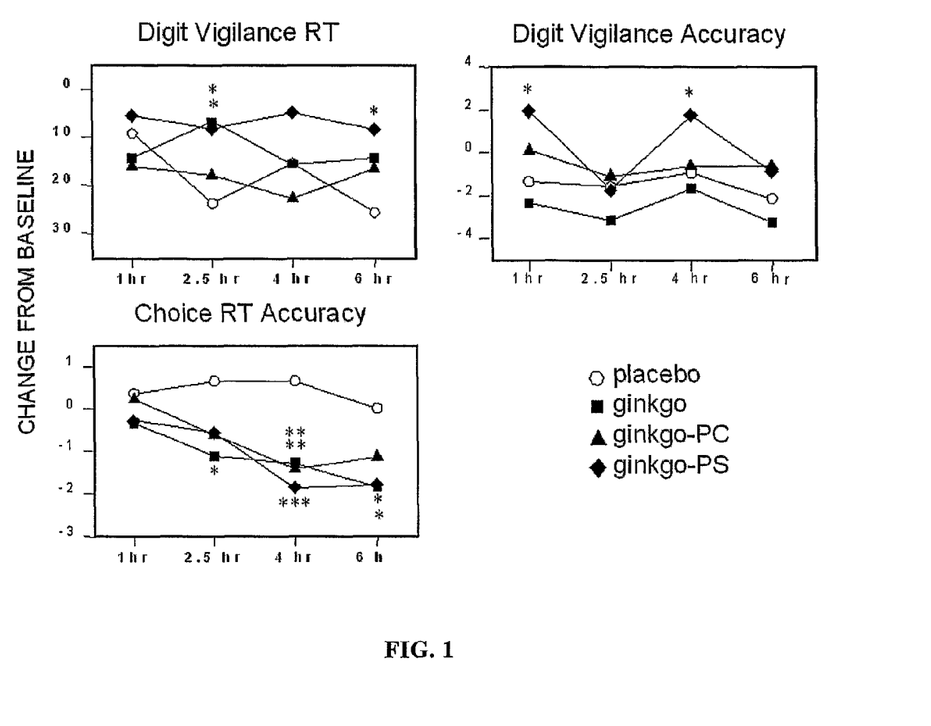
FIG. 1 shows the effects of individual tasks with regard to attention.
Figure 3:
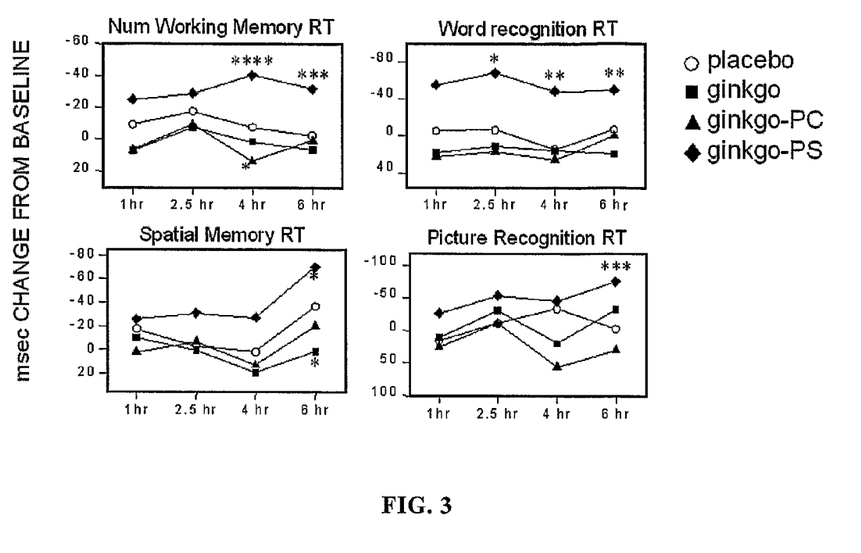
FIG. 3 shows the effects on timed memory tasks.
Figure 5:
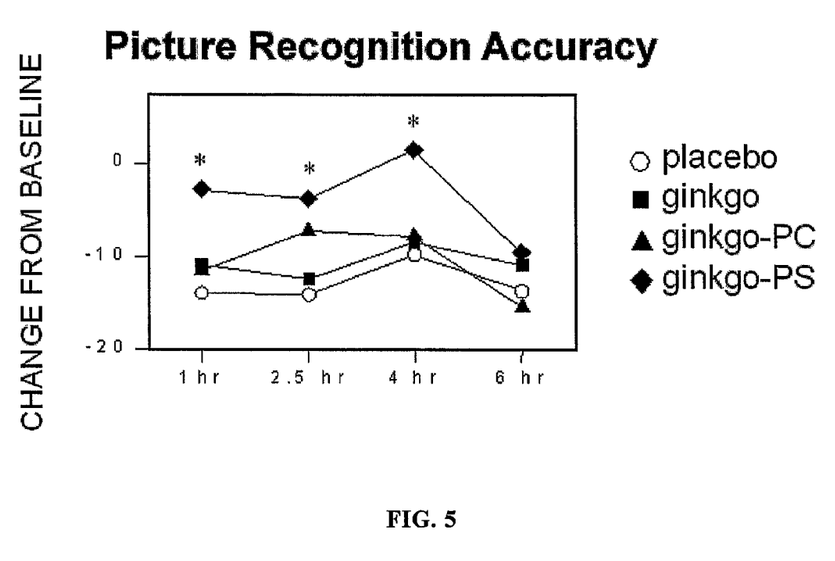
FIG. 5 shows the effects on picture recognition accuracy.
Figure 6:
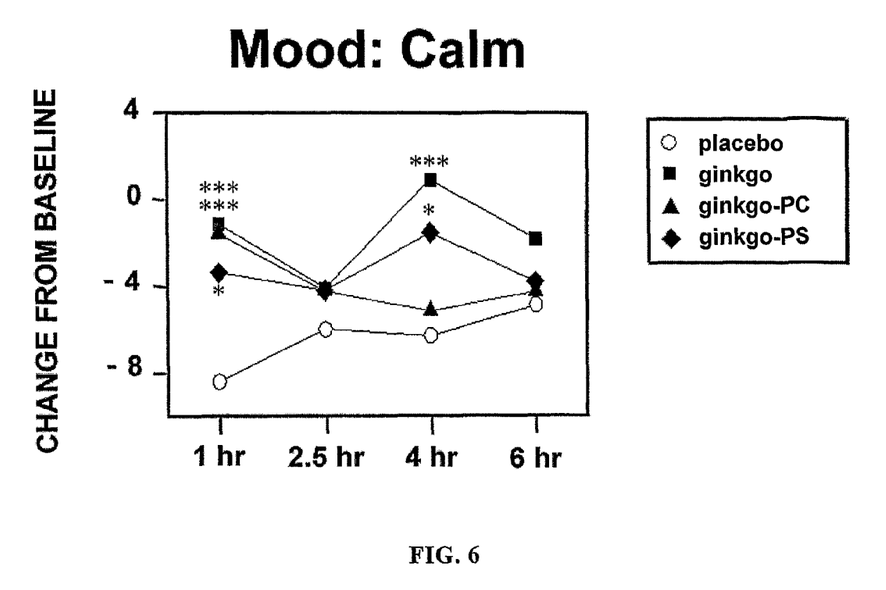
FIG. 6 shows and the effects found on mood "calm".

Effects and performance data on the individual task outcome measures from the CDR battery are shown in FIGS. 1, 3 and 5. Results of planned comparisons of individual task outcomes that generated a significant result on the initial ANOVA (statistic not reported) are described in relationship to the overall factor to which they contribute below. Mean baseline and change from baseline scores (with standard errors) are presented. Tasks are displayed in order of completion, with a graphical representation of measures generating significant differences on the initial ANOVA and subsequent planned comparisons (*, p=0.05; , p=0.01; *, p=0.005, *****, p=0.0005 compared to placebo).

Cognitive Factor Outcome Measures

Figure 2:
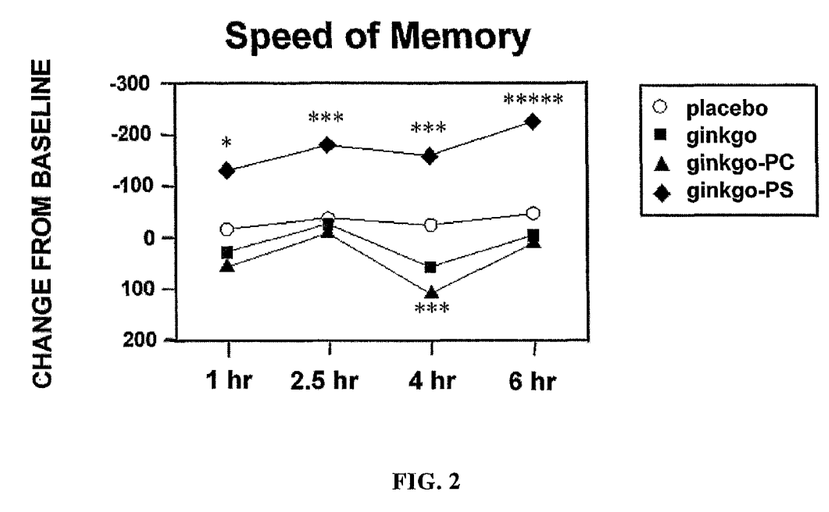
FIG. 2 shows the effects on speed of memory.
Figure 4:
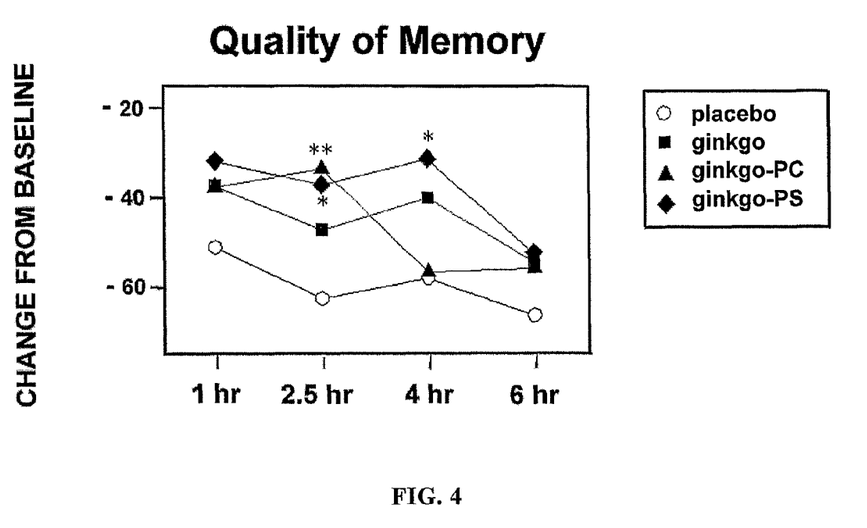
FIG. 4 shows the effects on quality of memory.

Effects of the treatments on the primary outcome cognitive factors derived from the CDR battery outcomes are shown in FIGS. 2 and 4. Mean baseline and change from baseline scores (with standard errors) are presented, with a graphical representation of the factors generating significant differences on the initial ANOVA and subsequent planned comparisons (*, p=0.05; , p=0.01; *, p=0.005, ****, p=0.001 compared to placebo).

Speed of Attention Factor (FIG. 1)

Whilst there was no significant difference on the primary outcome factor, a single component task outcome (digit vigilance reaction time) generated significant differences on the initial ANOVA and subsequent planned comparisons. Both ginkgo [t (243)=2.45, p=0.015] and ginkgo+PS [t (243)=2.25, p=0.026] performed significantly faster than placebo at 2.5 hours post-dose with the latter condition also performing faster at 6 hours [t (243)=2.5, p=0.013].

Accuracy of Attention Factor (FIG. 1)

Whilst there was no significant difference on the primary outcome factor, two single component task outcome (digit vigilance reaction time) generated significant differences on the initial ANOVA and subsequent planned comparisons. Accuracy of performing the Digit vigilance task was significantly improved for the ginkgo+PS condition at both 1 hour [t (243)=2.58, p=0.011] and 4 hours [t (243)=2.14, p=0.034] post-dose. In contrast to this all three doses evinced decrements in the accuracy of performing the Choice reaction time task with this effect being evident for ginkgo at 2.5 hours [t (243)=2.46, p=0.015], 4 hours [t (243)=2.66, p=0.009] and 6 hours [t (243)=2.56, p=0.011] post-dose, for ginkgo+PC at 4 hours post-dose [t (243)=2.86, p=0.005], and for ginkgo+PS at 4 hours [t (243)=3.45, p=0.001] and 6 hours [t (243)=2.46, p=0.015] post-dose.

Speed of Memory Factor (FIGS. 2 and 3)

The initial ANOVA showed that there was a significant main effect of the treatment on the Speed of Memory factor [F (3, 405)=15.76, p<0.001]. Planned comparisons showed that performance was enhanced at all time points following ginkgo+PS (1 hour [t (243)=2.58, p=0.011], 2.5 hours [t (243)=3.19, p=0.002], 4 hours [t (243)=3, p=0.003] and 6 hours [t (243)=4, p<0.001] post-dose). In contrast to this, performance was significantly slowed for the ginkgo+PC condition at 4 hours post-dose [t (243)=3, p<0.003].

Reference to the ANOVAS of the single outcomes contributing to this factor showed that performance was significantly modulated on all four tasks. Planned comparisons showed that following ginkgo+PS performance was faster on: the Spatial memory task at 6 hours [t (243)=2.23, p<0.027], with trends towards the same at 2.5 hours [t (243)=1.8, p=0.071],) and 4 hours [t (243)=1.92, p=0.056]; the Numeric working memory task at 4 hours [t (243)=3.29, p=0.001] and 6 hours [t (243)=2.944, p=0.004]; the Word recognition task at 1 hour [t (243)=2.2, p=0.028], 2.5 hours [t (243)=2.75, p=0.006], and 4 hours [t (243)=2.77, p=0.006], with a trend towards the same at 6 hours post-dose [t (243)=1.91, p=0.057]; and the Picture recognition task at 6 hours [t (243)=3.12, p=0.002], with trends towards the same at 1 hour [t (243)=1.75, p=0.082] and 2.5 hours [t (243)=1.82, p=0.071].

In contrast to these marked improvements both of the other conditions were associated with the occasional decrement, with ginkgo evincing slowed performance on the Spatial memory task at 6 hours [t (243)=2.56, p=0.011], and the Picture recognition task at 4 hours [t (243)=2.25, p=0.026], and ginkgo+PC evincing slowed performance on the Numeric working memory task at 4 hours [t (243)=2.15, p=0.033] and the Picture recognition task at 4 hours post-dose [t (243)=3.8, p<0.001].

Quality of Memory Measure (FIGS. 4 and 5)

The initial ANOVA showed that there was a significant main effect of treatment on the global Quality of Memory measure [F (3, 405)=3.33, p=0.02]. Planned comparisons showed that ginkgo+PS resulted in improved change from baseline performance at 2.5 hours [t (243)=2.35, p=0.02] and 4 hours [t (243)=2.46, p=0.015] with a trend towards the same at 1 hour [t (243)=1.78, p=0.077] post-dose. Performance was also enhanced for ginkgo+PC at 2.5 hours [t (243)=2.67, p=0.008].

Reference to the contributing single task outcomes showed that performance was only significantly improved on one individual task outcome task, with ginkgo+PS outperforming placebo at 1 hour [t (243)=2.39, p=0.018], 2.5 hours [t (243)= 2.24, p=0.027] and 4 hours [t (243)=2.43, p=0.016] on the Picture recognition task.

Secondary Memory Factor

The initial ANOVA suggested that this factor was not significantly affected by the treatment.

Working Memory Factor

The initial ANOVA suggested that this factor was not significantly affected by the treatment.

Serial 7s and Serial 3s Subtraction Tasks

The initial ANOVA suggested that these tasks were not significantly affected by the treatments.

Mood Assessment

The changes from baseline scores for the three mood factors (alert, content, calm) are evaluated. FIG. 5 illustrates the effects of the treatments on the mood factor 'calm' derived from the Bond-Lader mood scales. Mean baseline and change from baseline scores (with standard errors) are presented, with a graphical representation of the factor that generated significant differences on the initial ANOVA and subsequent planned comparisons (*, p=0.05; , p=0.01; *, p=0.005, **, p=0.001,***, p=0.0005 compared to placebo).

Bond-Lader Mood Scales (cf. FIG. 5)

The initial ANOVA suggested that there was only a main effect of treatment on the "Calm" factor derived from the visual analogue scales [F (3, 405)=2.95, p<0.032]. Planned comparisons revealed that all three treatments resulted in enhanced "calmness" in comparison to placebo. This effect was evident for ginkgo at 1 hour [t (243)=3.05, p=0.003] and 4 hours [t (243)=3.02, p=0.003], ginkgo+PC at 1 hour [t (243)=2.87, p=0.005], and ginkgo+PS at 1 hour [t (243)=2.1, p=0.036] and 6 hours [t (243)=1.99, p=0.048] post-dose.

SUMMARY OF THE EFFECTS

It has been found that the ginkgo phosphatidylserine complex used according to the present invention has an outstanding higher effectivity compared with the other tested species, i.e. not complexed ginkgo or ginkgo phosphatidylcholine complex, regarding Quality of Memory, Picture Recognition Accuracy, Speed of Memory, Timed Memory Tasks and the majority of the tasks concerning attention.

The invention claimed is:

1. A method for enhancing cognitive function and alleviating mental fatigue in a subject, comprising administering to a subject in need thereof an effective amount of a *Ginkgo*-phospholipid complex, said complex comprising *Ginkgo* complexed with a phospholipid, said phospholipid comprising 20% phosphatidylserine.

2. The method according to claim 1, wherein the *Ginkgo* is derived from the plant *Ginkgo biloba*, extracts thereof and/or one or more principal active substances thereof.

3. The method according to claim 2, wherein one of the principal active substances is bilobalide.

4. The method according to claim 2, wherein the *Ginkgo* extract comprises at least 20% *Ginkgo* flavone glycosides and 2-10% terpene lactones.

5. The method according to claim 1, wherein the *Ginkgo* and the phosphatidylserine in the complex are in a ratio of about 1:3.

6. The method according to claim 1, wherein the *Ginkgo*-phospholipid complex is in a medicament or a dietary supplement that is administered to the subject in the form of tablets, granules, powders, capsules, syrups, solutions, suspensions, dragees, gels, injections or drops.

7. The method according to claim 1, wherein the *Ginkgo*-phospholipid complex is in a medicament or a dietary supplement and is formulated for oral administration.

8. The method according to claim 1, wherein the *Ginkgo*-phospholipid complex is in a medicament or a dietary supplement that is administered in an amount of about 20-240 mg per day.

9. The method according to claim 1, wherein the *Ginkgo*-phospholipid complex is in a medicament or a dietary supplement, and further comprises a pharmaceutically acceptable amount of at least one additive selected from the group consisting of minerals, vitamins, sweeteners, flavors, pharmaceutically acceptable carriers, auxiliary and binder agents, excipients and mixtures thereof.

10. The method according to claim 9, wherein the additive is selected from the group consisting of calcium, fluorine, phosphorus, copper, potassium, manganese, magnesium selenium, zinc and iron, Vitamin A, Vitamins B1, B2 and B12, Vitamin C, Vitamin D2, nicotinamide, calcium pantotenate, rutoside and Vitamin E.

11. The method according to claim 1, wherein the *Ginkgo* and phosphatidylserine in the complex are in a ratio of 0.5-1:2-5.

12. A method for improving memory speed and memory quality in a normal, healthy human, or reducing deterioration of memory speed and memory quality in a human with decreased cognitive functions, comprising administering to a subject in need thereof an effective amount of *Ginkgo* complexed with phosphatidylserine.

13. A method for treating a disease related to reduced cognitive function and increased mental fatigue in a subject, comprising administering to a subject in need thereof an effective amount of *Ginkgo* complexed with phosphatidylserine.

14. The method according to claim 13, wherein the disease is Dementia.

15. The method according to claim 13, wherein the disease is Alzheimer's Disease.

16. The method according to claim 13, wherein the *Ginkgo*-phosphatidylserine complex is in a medicament or a dietary supplement, and further comprises a pharmaceutically acceptable amount of at least one additive selected from the group consisting of vitamins, minerals, sweeteners, flavors, pharmaceutically acceptable carriers, auxiliary and binder agents, excipients and mixtures thereof.

17. The method according to claim 13, further comprising administering an additional pharmaceutical compound used for treating the disease related to reduced cognitive function and increased mental fatigue.

18. The method according to claim 17, wherein the additional pharmaceutical compound is an acetylcholinesterase inhibitor.

19. The method according to claim 13, further comprising administering complexed grape seed extract, as an additionally active compound, to the subject.

* * * * *

UNITED STATES PATENT AND TRADEMARK OFFICE
CERTIFICATE OF CORRECTION

PATENT NO. : 8,591,965 B2  Page 1 of 1
APPLICATION NO. : 10/587468
DATED : November 26, 2013
INVENTOR(S) : Morazzoni et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1735 days.

Signed and Sealed this
Twenty-second Day of September, 2015

Michelle K. Lee
*Director of the United States Patent and Trademark Office*